United States Patent [19]

Man

[11] Patent Number: Plant 6,322

[45] Date of Patent: Oct. 4, 1988

[54] DISTINCT VARIETY OF BEGONIA PLANT NAMED ROSANNA

[75] Inventor: Jan Man, Lisse, Netherlands

[73] Assignee: Oglevee Associates, Inc.

[21] Appl. No.: 885,549

[22] Filed: Jul. 14, 1986

[51] Int. Cl.[4] ..... A01H 5/00
[52] U.S. Cl. ..... Plt./68
[58] Field of Search ..... Plt./68

*Primary Examiner*—Robert E. Bagwill
*Attorney, Agent, or Firm*—Webb, Burden, Robinson & Webb

[57] ABSTRACT

A new Begonia variety is characterized by its pastel pink blooms which are numerous and long lasting. The plants exhibit superior vigor and strength. The new cultivar has a high tolerance to botrytis and powdery mildew.

1 Drawing Sheet

BACKGROUND OF THE NEW PLANT

The present invention comprises a new and distinct cultivar of *Begonia*×*hiemalis* known by the varietal name of Rosanna. The new cultivar is a natural sport of the cultivar Rosalie. The new cultivar has the same plant foliage and form as Rosalie, but the tonality of Rosalie is a peach to light orange whereas the tonality of Rosanna is pink.

The new cultivar was discovered at Limaplant b.v. in Lisse, Holland; was first asexually reproduced by cuttings at Limaplant b.v. in Lisse, Holland; and has been repeatedly asexually reproduced by cuttings for Oglevee Associates, Inc. in Connellsville, Pa. It has been found to retain its distinctive characteristics through successive propagations.

The new cultivar is generally characterized by its pastel pink blooms which are numerous and long lasting. The plants exhibit superior vigor and strength. The new cultivar has a high tolerance to botrytis and powdery mildew.

The new cultivar, when grown in a greenhouse in Connellsville, Pa. has a response time of 10 to 11 weeks from a well-rooted cutting to a flowering finished plant in a six inch pot (no pinch).

DESCRIPTION OF THE DRAWING

The accompanying drawing illustrates a new cultivar, the color being as nearly true as possible with color illustrations of this type.

DESCRIPTION OF THE NEW PLANT

The following detailed description sets forth the characteristics of the new cultivar. The data which define these characeristics were collected from asexual reproductions carried out for Oglevee Associates, Inc. in Connellsville, Pa. The plant history was taken on ten week plants blossomed under natural light in a greenhouse and grown under temperature conditions of 62° F. at night and 68° F. during the day. The plants were potted in a peat-lite mix and fertilized with a 100 ppm mixture of 15N-0P-15K. Color readings were taken indoors under 200 footcandles of cool white fluorescent tubes. Color references are to the R.H.S. Colour Chart of The Royal Horticultural Society of London, unless noted differently.

Botanical classification: *Begonia*×*hiemalis.*

Flower:

*Fully expanded.*—4 cm in diameter.

*Buds.*—2 cm wide.

*Borne.*—Compound dichasium (cyme).

*Stems.*—Peduncles are strong and upright; main peduncle 4 mm in diameter; color yellow-green group 145B.

*form.*—Semi-double to fully double. Each flower generally has 2 sepals, 7 petals, 7 petaloids (each group may vary±1 structure).

*Permanence.*—Long lasting bloom, generally each bloom will last 2–3 weeks.

Color:

*Tonality from a distance.*—Pink.

*Bract.*—Characterized by a color yellow-green group 144C with margin being translucent.

*Calyx.*—Front of calyx: In the mature form the margin and outer portions are characterized by color red group 49A. Approaching the base of sepal the color lightens to green group 142D. Reverse of calyx: In the bud stage the color is characterized as a solid yellow-green group 145C and with maturity the outer edges become more pink characterized as a red group 49B.

*Petal.*—Front of petals: Fully mature and expanded, is characterized by the color red group 50C with the extreme base of the petal characterized as green group 142D. Reverse of petals: Fully mature and expanded is characterized by the color red group 49B with the base of the petal characterized as green-white group 157C. Base of petals: Yellow-green 142D. Throat: None. Discoloration: None. Other comments: With maturity the tonality of the petals intensifies. Immature and not fully expanded petals are characterized by a lighter color than the mature fully expanded petals. The perceived appearance of a yellow eye in the center of the flower cluster is the result of the arrangement of the light green base (green group 142D) of the petaloid. Additionally the calyx has a tendency to revert to a green chemical.

Petals:

*Texture.*—Crepe paper like (gentle crinkles).

*Appearance.*—Generally balloon shaped (less than other Lima Begonia) Color gradient→edge: dark pink→light pink→very light pink (almost white).

*Arrangement.*—Semi-double to fully double.

*Persistence.*—Fairly persistent, long lasting bloom, high number of buds.

*Fragrance.*—None.

Reproductive organs: All reproductive organs have modified into petaloids. Anthers, filament, pollen and style could not be observed.

Plant:

*Form.*—Compact, close internodes (2–3 cm apart); upright, good self-support, good basal branching.

*Growth.*—Vigorous; plant growth can be modified by changing environmental conditions in which the plant is grown (higher temperatures yield faster, more lush growth).

*Height from soil line.*—20–22 cm in 11 weeks (no pinch, no cycocel).

*Spread.*—34–36 cm in 11 weeks (no pinch, no cycocel).

Foliage:

*Size.*—Depends on how plant was grown, age and position of leaf on plant. Average length of 11 cm and average width of 9 cm.

*Quantity.*—Very abundant.

*Shape.*—Acute tip with irregularly lobed petiole attachment; edge is doubly serrated.

*Top side.*—Green group 137B.

*Underside.*—Green group 138B to 138C.

*Ribs and veins.*—Palmate arrangement, smooth on top, raised on bottom, lower side veins only area where tricomes appear.

*Rib and vein color.*—Top side: yellow-green group 145B; bottom side: yellow-green group 147D.

*Margin.*—None.

*Stipules.*—None.

*Texture.*—Top: smooth, shiny glabrous; bottom: matt finish with raised veins.

I claim:

1. A new and distinct variety of Begonia characterized by its pastel pink blooms which are numerous and long lasting, superior vigor and strength and high tolerance to botrytis and powdery mildew as herein shown and described and parts therefor.

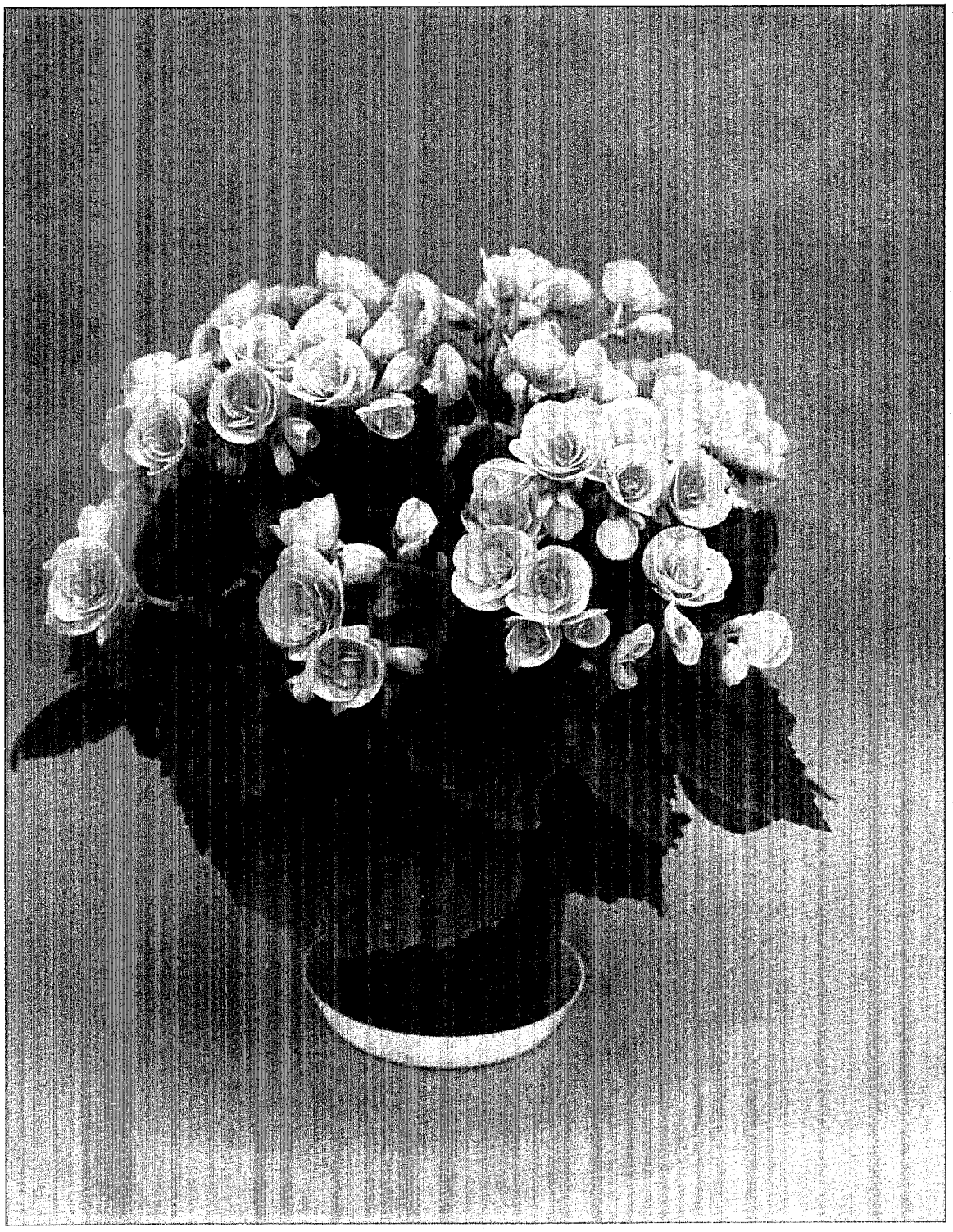

* * * * *